United States Patent [19] [11] 4,038,982
Burke et al. [45] Aug. 2, 1977

[54] ELECTRICALLY CONTROLLED INTRAVENOUS INFUSION SET

[75] Inventors: George K. Burke; Robert J. LeFevre, both of Bethlehem; Robert E. Thomas, Wind Gap; James W. Turner, Bethlehem; Peter L. Krohn, Easton, all of Pa.

[73] Assignee: Burron Medical Products, Inc., Bethlehem, Pa.

[21] Appl. No.: 637,208

[22] Filed: Dec. 3, 1975

[51] Int. Cl.² ............................................. A61M 5/14
[52] U.S. Cl. ...................... 128/214 E; 128/DIG. 13; 137/487.5; 222/52; 222/76; 250/205; 250/222 PC; 250/573
[58] Field of Search ........... 128/214 R, 214 C, 214 E, 128/214 F, 214.2, DIG. 12, DIG. 13; 251/123-125, 139, 141; 137/486, 487.5; 222/52, 59, 76, 420, 422; 73/194 E; 250/205, 222 PC, 564, 573; 356/102

[56] References Cited

U.S. PATENT DOCUMENTS

| 3,163,176 | 12/1964 | Darling | 137/487.5 |
|---|---|---|---|
| 3,252,623 | 5/1966 | Corbin et al. | 222/59 |
| 3,563,090 | 2/1971 | Deltour | 73/194 E |
| 3,609,379 | 9/1971 | Hildebrandt | 250/364 |
| 3,631,250 | 12/1971 | Van Buskirk | 250/205 |
| 3,800,147 | 3/1974 | Shea et al. | 250/205 X |
| 3,859,539 | 1/1975 | Allington | 250/205 X |
| 3,884,228 | 5/1975 | Hahn | 128/214 F |
| 3,890,968 | 6/1975 | Pierce et al. | 128/214 E |
| 4,001,801 | 1/1977 | Moulet | 128/214 E X |

Primary Examiner—Dalton L. Truluck
Attorney, Agent, or Firm—Shoemaker and Mattare, Ltd.

[57] ABSTRACT

An electronically controlled intravenous infusion set of the gravity feed type having a flow path including a drip chamber and an internal valve for regulating flow through the set. Electromagnetic valve operating structure, positioned outside the IV set, controls the internal valve in response to an electronic control system. The electronic control system serves to open the valve to allow a drop to fall, and includes a control circuit. The control circuit includes an optical drop detector, associated with but positioned outside the drip chamber, which senses the falling drop and signals the control circuit to close the valve. The control circuit also includes a variable frequency clock and associated digital selectors for affording an attendant the ability to precisely select a desired drip rate. An alarm system, operating on digital principles, senses high drop rate or low drop rate conditions and, in response thereto, puts the control system into an alarm condition. The alarm system includes means for digitally adjusting the sensitivity thereof to provide high sensitivity at low drip rates but to decrease the sensitivity at higher rates so that premature alarm conditions are avoided.

25 Claims, 10 Drawing Figures

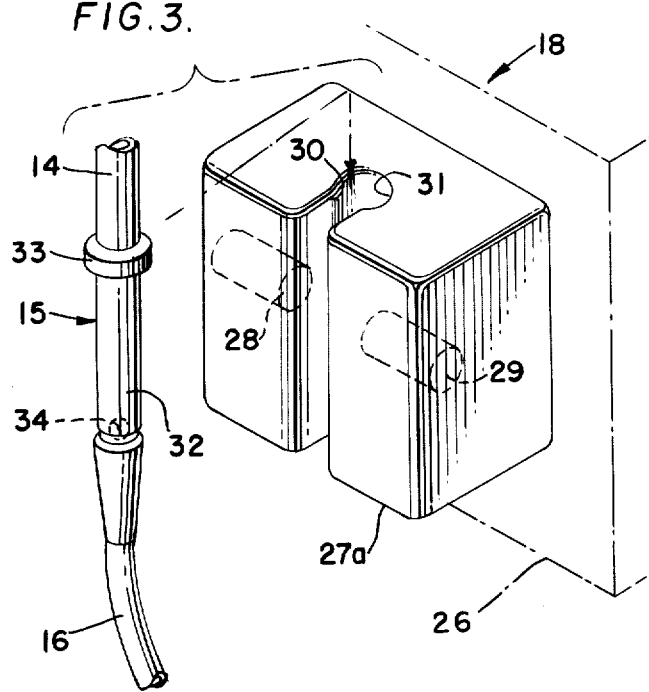
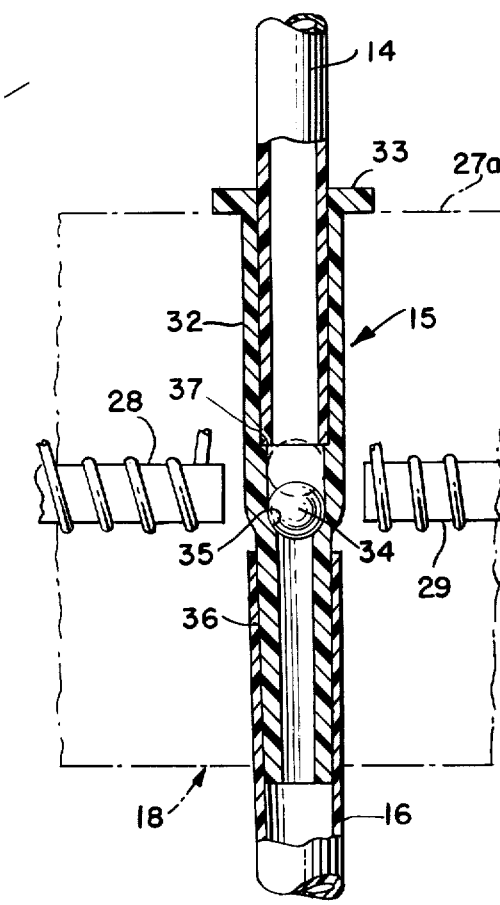
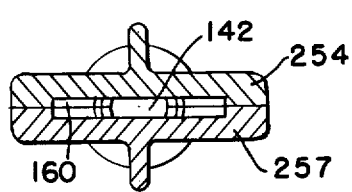
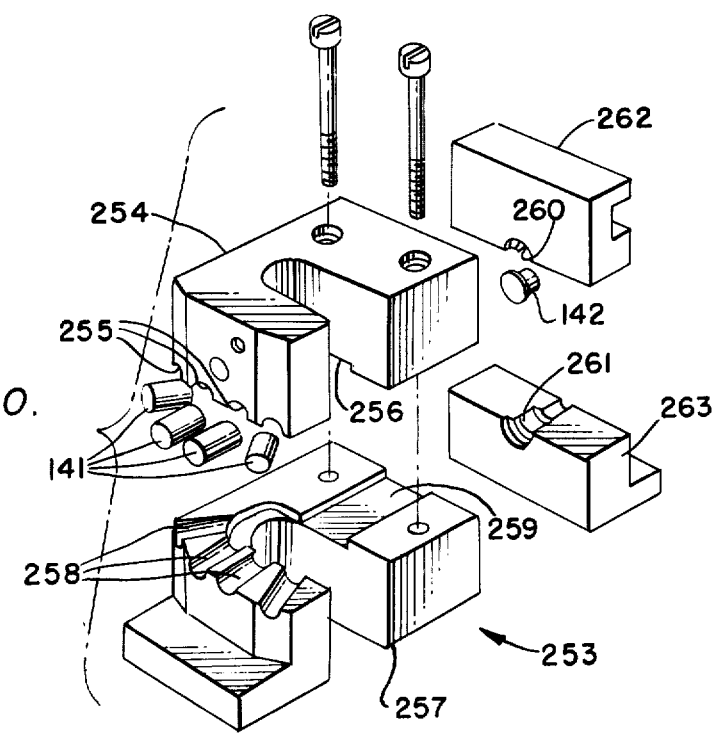

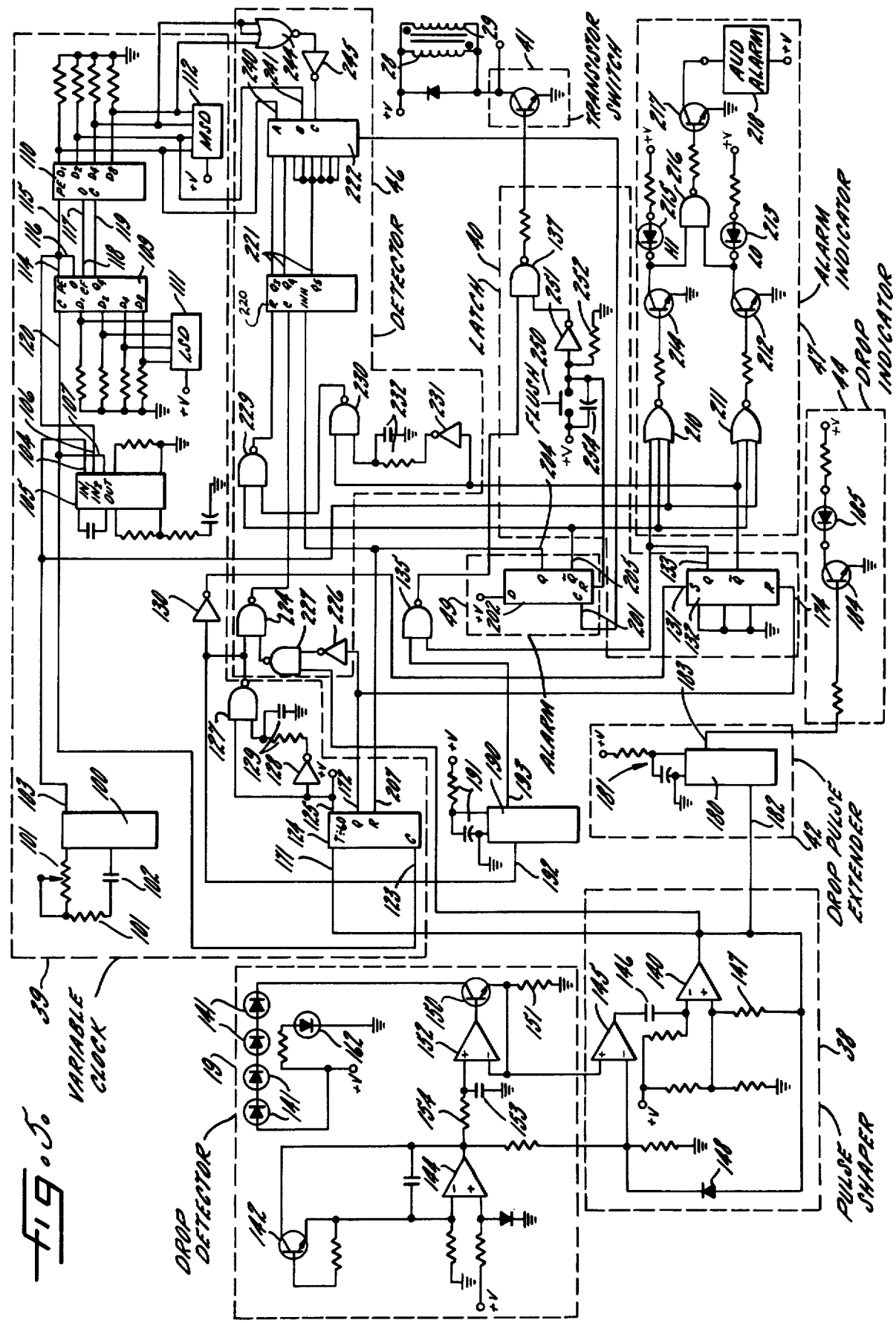

ELECTRICALLY CONTROLLED INTRAVENOUS INFUSION SET

BACKGROUND OF THE INVENTION

This invention relates to intravenous infusion sets (IV sets) of the gravity feed type, and more particularly to such sets including electronic control systems for establishing the drip rate and monitoring said rate to detect alarm conditions. Even more specifically, this invention relates to improvements in the electronically controlled IV set disclosed in copending LeFevre Application Ser. No. 492,280, assigned to the same assignee as the present invention, and now abandoned in favor of Application Ser. No. 637,206, filed Dec. 3, 1975.

The prior art includes numerous means for controlling the rate of flow through IV sets for regulating the rate of intravenous administration of fluid to a patient. The rate, for example, may be controlled manually by adjusting a mechanical clamp on the IV tubing while counting drops falling in the drip chamber over a predetermined period of time to achieve a desired drop rate. Electronic controls have been developed to eliminate this time consuming and error prone manual procedure. Such systems generally include a valve operating within or upon the IV tubing and a circuit for controlling the valve to establish a desired flow rate. Many of such circuits also incorporate drop detectors for sensing a drop forming or falling in the drip chamber. While the electronic IV controls known heretofore have generally represented a considerable improvement over prior manual techniques, they have not been altogether successful in allowing an attendant to precisely select a drip rate and thereafter precisely maintaining such rate. For example, it has been common to select the flow rate in electronic IV sets using conventional dial type selectors, such an approach having an inherent accuracy limitation. Further, some prior art devices operate flow control valves at some multiple frequency of a desired drop rate, in order to control the flow rate through the set.

Problems also exist in the prior art with regard to alarm systems associated with the electronic control. In some cases, the alarm systems may be made "hair trigger" responsive, causing an alarm upon the detection of only a single error or missed drop. In other cases a deadband is established in which errors may occur without causing an alarm. The former systems are prone to premature alarm conditions, especially at high flow rates where the occasional error may be tolerated. The latter systems may be found to be too insensitive, especially at low flow rates.

OBJECTS OF THE INVENTION

In view of the foregoing, it is a general object of the present invention to provide an electronically controlled IV set for precisely controlling the drip rate and including selector means for affording an attendant the ability to precisely establish the drip rate. In that regard, it is an object of the invention to provide such an IV set including a variable frequency clock settable by user operated digital switches for precisely selecting the drip rate.

According to another feature of the invention, it is an object to provide an electronically controlled IV set including an alarm system wherein the sensitivity of the alarm system is varied in accordance with the drip rate. It is a detailed object to provide such an alarm system with high sensitivity at low flow rates but with an increasing error deadband at higher flow rates. Even more specifically, it is an object to provide a digital alarm system for counting errors, and means responsive to the number of errors counted and to the preselected flow rate for switching the control into the alarm mode.

According to a still further feature of the invention, it is an object to provide an electronically controlled IV set having a drop detector which functions not only to sense each drop falling in the drip chamber, but also adjust itself for varying opacity of the drip chamber, such as might be caused by fogging thereof. Even more specificlly, according to this aspect of the invention, it is an object to provide such a drop detector including a light emitter and a photosensitive device wherein the photosensitive device serves not only to sense falling drops but also to control the intensity of light produced by the light emitter.

Other objects and advantages will become apparent from the following detailed description, when taken in conjunction with the drawings, in which:

FIG. 3 is a perspective, exploded view showing the IV set with internal valve and the valve operating mechanism;

FIG. 4 is an enlarged, sectional view showing the valve of FIG. 3 and its relationship with the valve operating mechanism;

FIG. 5 is a schematic diagram illustrating a control circuit exemplifying the present invention;

FIG. 9 is a view in section taken along line 9—9 of FIG. 7;

FIG. 10 is an exploded, perspective view of the drop detector housing or case assembly.

DETAILED DESCRIPTION OF THE PREFERRED EMBODIMENTS

While the invention will be described in connection with certain preferred embodiments, it will be understood that there is no intent to limit it to those embodiments. On the contrary, the intent is to cover all alternatives, modifications and equivalents included within the spirit and scope of the invention as defined by the appended claims.

Figure 1:
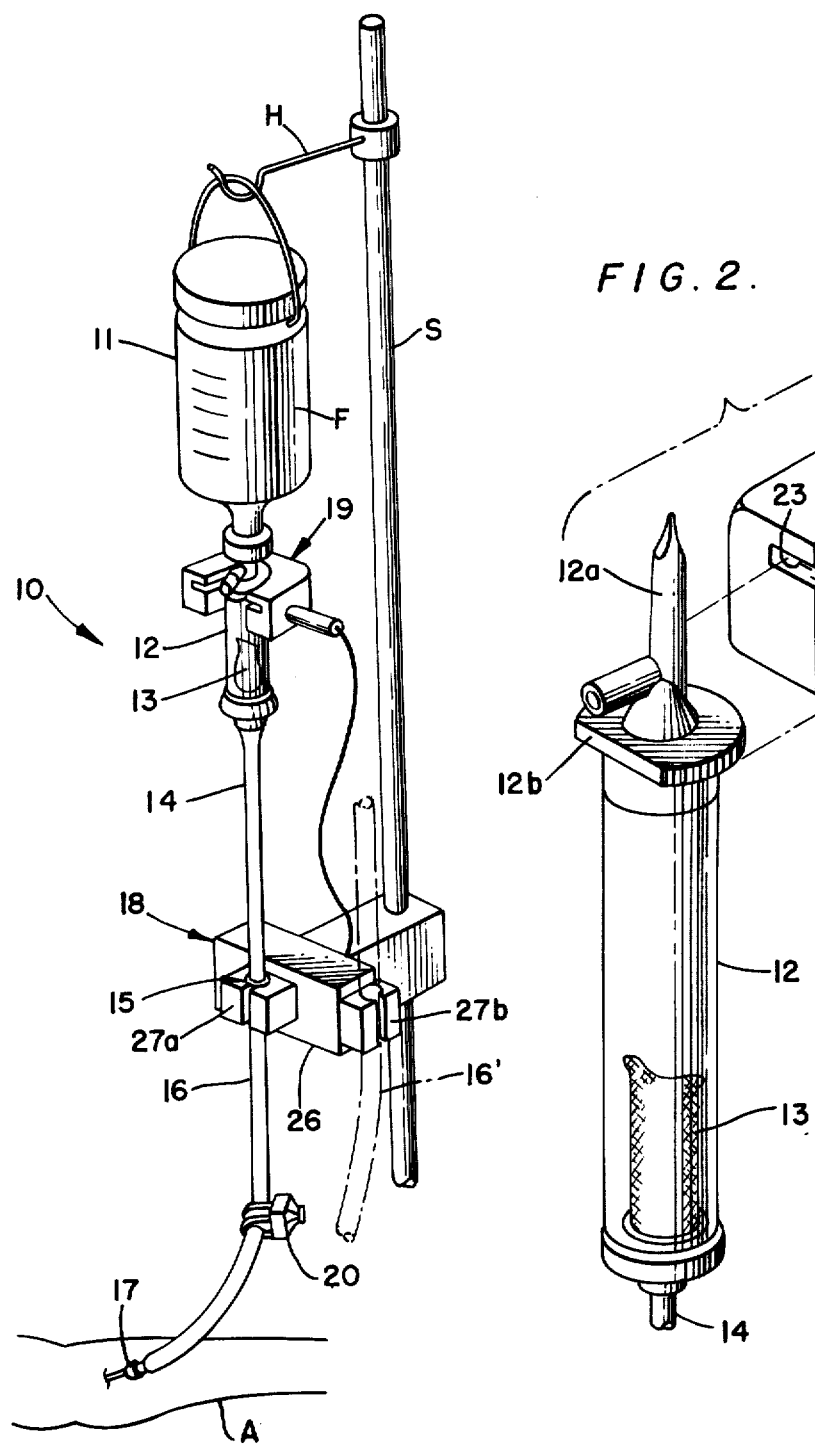
FIG. 1 is a perspective view of an IV set including an electronic control system exemplifying the present invention.

Turning now to the drawings, FIG. 1 shows an IV set, generally indicated at 10, for controlling the flow of intravenous fluid to a patient. A supply 11 of intravenous fluid F, in the form of a bottle, bag, or the like, is suitably suspended or supported from a hook H carried by an upright post or support S. A drip chamber 12 is connected to the bottom of the supply 11 in a conventional manner; typically the drip chamber 12 has a piercing end 12a thereon (FIG. 2) which is inserted into the bottom end of the supply 11. A suitable filter 13 is preferably provided in the drip chamber 12 for filtering contaminants from the fluid F.

For controllably conducting the intravenous fluid to a patient, the fluid supply is connected to a length of IV tubing having an internal valve, shown herein as a first length of tubing 14, a second length of tubing 16 and a valve 15 interposed therebetween. Connected to the end of the fluid flow passage defined by the drip chamber and IV tubing with internal valve is a needle 17 for insertion into the arm A of a patient for intravenous administration of fluids to the patient.

For controlling the operation of the internal valve 15, an electronic control, generally indicated at 18, is operatively associated with the valve and is adapted to open such valve at a rate preselected by an attendant. A drop detector 19, positioned proximate the drip chamber 12 for sensing each drop of fluid F falling through the drip chamber, is connected to the electronic control for providing a feedback signal to cause the closing of the valve. If desired, a manually operated clamp 20 of conventional construction may be positioned on the IV tubing to allow manual control of the drip rate. In this event, means such as a permanent magnet (not shown) is positioned to hold the valve open.

Figure 2:
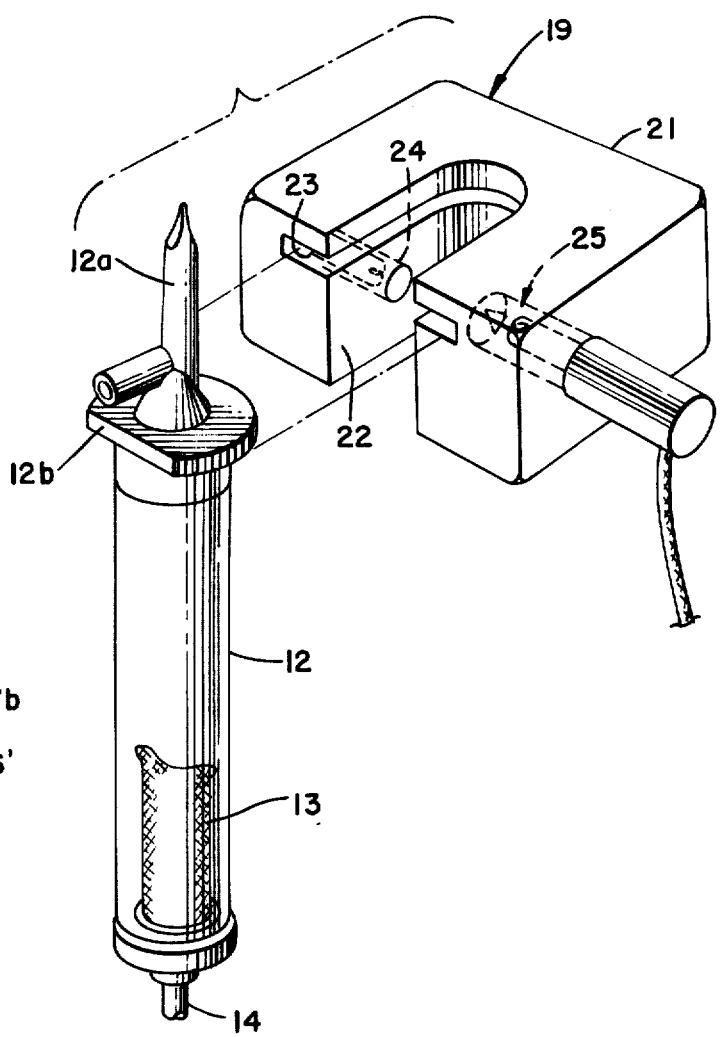
FIG. 2 is an exploded view showing the drop detector with drip chamber removed.
Figure 6:
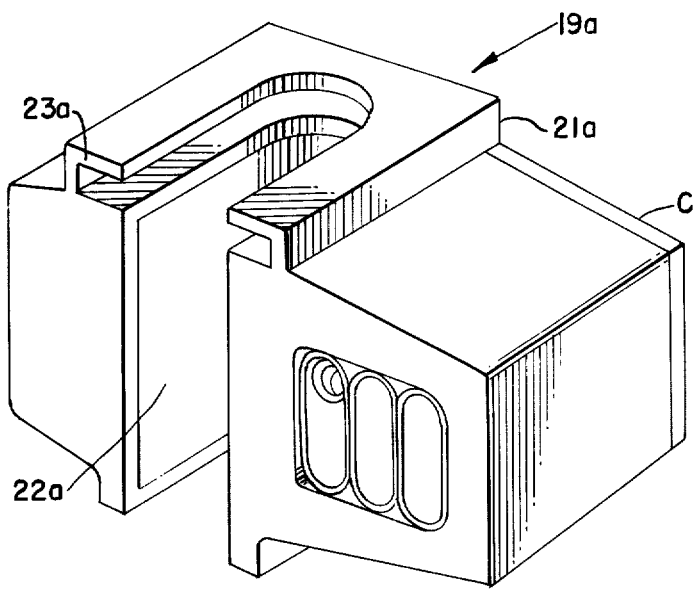
FIG. 6 is a perspective view of an alternative form of drop detector.
Figure 7:
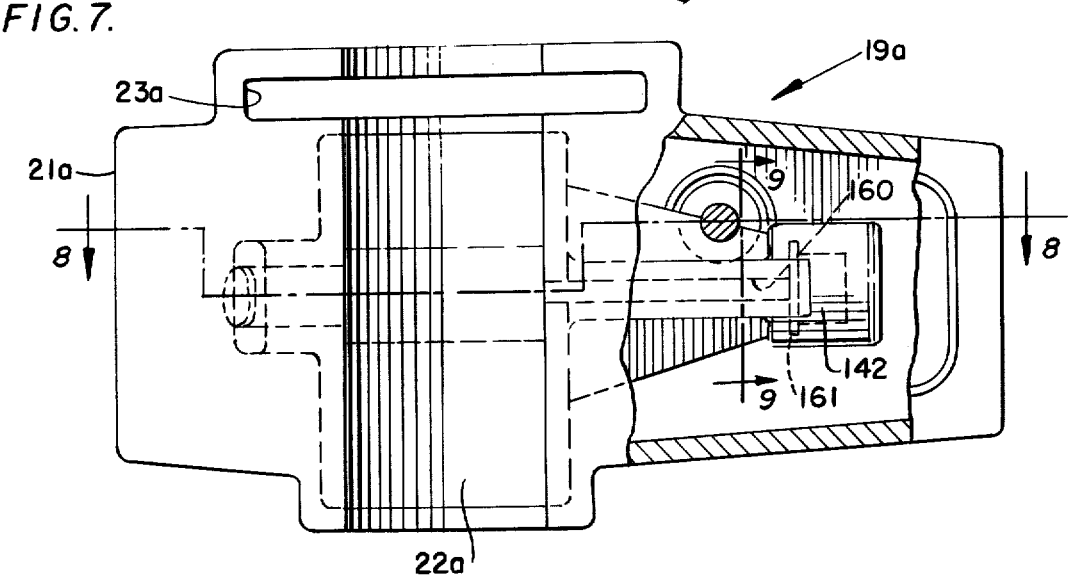
FIG. 7 is a front elevational view of the drop detector of FIG. 6.
Figure 8:
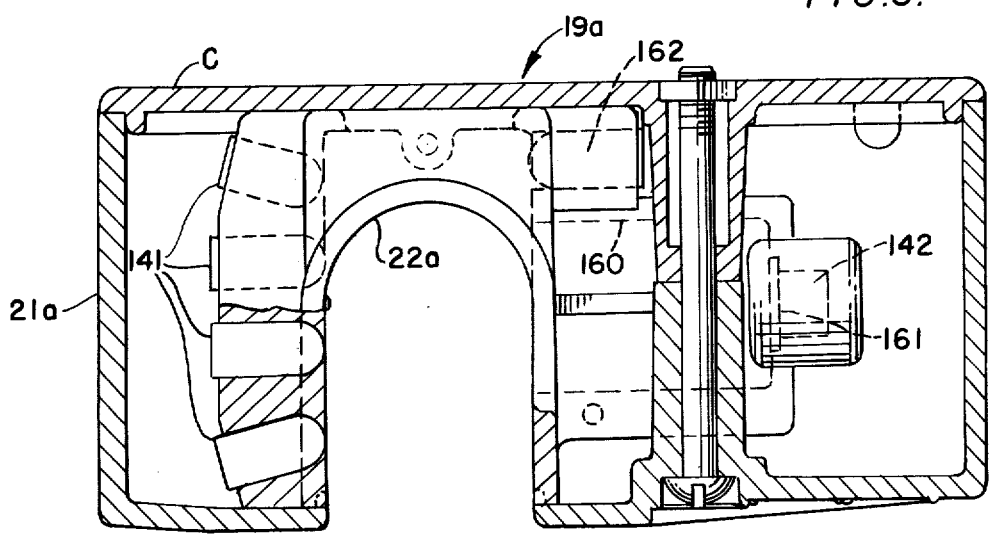
FIG. 8 is a sectional view taken along lines 8—8 of FIG. 7.

The drop detector 19, shown in greater detail in FIG. 2, is preferably of molded plastic and comprises a generally U-shaped housing 21 having an elongated slot 22 in one side thereof, with a generally U-shaped channel or groove 23 in the body extending around the slot 22 adjacent the upper portion thereof. A light source 24 is positioned in the housing and is opposed by a light sensor 25, these elements being optically coupled such that any drop of liquid falling through the drip chamber 12 will interfere with the light beam from the source 24 to the sensor 25. In use, the drop detector 19 is mounted to the drip chamber 12 by inserting the drip chamber into the slot 22 with the flange 12b at the upper end of the drip chamber received in the groove 23 in the housing 21. In this position, the light source 24 will be on one side of the drip chamber and the opposed light sensor 25 on the other side thereof so that a drop falling through the drip chamber will interrupt the beam of light. It will now be apparent that this arrangement causes the sensor 25 to produce a signal in response to each falling drop, such signal being coupled to the control circuit as noted above.

The electronic control 18 is preferably housed within a suitable control box 26 and includes a valve operating mechanism mounted within a housing 27a. More specifically, and as shown in greater detail in FIG. 3, the housing 27a includes a pair of electromagnets 28, 29 disposed on opposite sides of a slot 30 formed in the housing. The slot is slightly enlarged at the closed portion 31 thereof and is so sized in relation to the valve 15 that the valve may be inserted through the slot 30 and pulled downwardly into the enlarged portion 31 with a shoulder 33 seating atop the housing 27a.

The valve preferably comprises a one piece, elongate, plastic, tubular valve body 32 having the aforementioned shoulder 33 at the upper end thereof arranged to properly locate the valve and valve ball 34 contained within relative to the electromagnets 28, 29. The valve body 32 is tapered inwardly between its ends to define an upwardly facing valve seat 35 against which the valve ball 34 seats under the action of gravity and the pressure of fluid above the valve. The lower end 36 of the valve body is gradually inwardly tapered for reception thereover of the end of IV tubing section 16. The inlet section 14 of IV tubing is secured within the upper portion of the valve body 32, and the lower end of the IV tubing 14 is abutted against a narrow, annular, upwardly facing shoulder 37 in the bore of the upper portion of body 32 to correctly space the end of the IV tubing 14 from the ball valve 34.

As shown in FIG. 1, a permanent magnet housing 27b may be provided on the control unit 18, shaped substantially like the electromagnet housing 27a, but containing a pair of permanent magnets in place of the electromagnets. Thus, if it is desired to flush the set, the valve means 15 is merely placed in position in housing 27b, the permanent magnet serving to hold the valve open, causing full flow through the set. Moreover, in the event it is desired to bypass the electronic control and utilize the IV set with manual control, the valve means may be positioned in the permanent magnet housing to thus hold the valve open, and the clamp 20 adjusted to obtain the desired drip rate.

In accordance with the invention, a completely digital solid state control is provided for operating the valve means, an exemplary embodiment of such control being illustrated in FIG. 5. The control circuit includes a variable clock 39, digitally settable, to allow an attendant to precisely select a desired drip rate. Clock pulses at the selected frequency, one pulse per desired drop, are fed to a latching circuit 40 driving a transistor switch 41, the electromagnets 28, 29 being connected in the load circuit of the switch 41. As a result, the occurrence of a clock pulse will cause the latching circuit 40 to energize the transistor switch 41, causing current flow through the electromagnets 28, 29 and lifting the ball 34 from its seat in the valve. The drop detector 19, the circuitry of which is illustrated in the left hand portion of FIG. 5, senses the falling drop and produces a signal in response thereto which resets the latching circuit 40 causing it to deenergize the switch 41, ceasing the flow of current through the electromagnets 28, 29 and allowing the ball 34 to return to its seat under the force of gravity and fluid pressure.

For providing an indication of operation to an attendant, a drop pulse extender 42 responds to the signal produced by the drop detector 19, as shaped by pulse shaper 38, to drive a drop indicator 44, thereby flashing an indicator for each drop falling through the drip chamber.

Alarm detector circuitry 46 monitors the signals produced by the clock 39 and the drop detector 19 and, in response to abnormal conditions detected from said signals causes the control system to enter the alarm mode. In short, the clock 39 and drop detector 19 form two inputs to the alarm detector, the detector serving to sense successive pulses from one of said sources without an intervening pulse from the other source, such condition being defined as an error. More specifically, if two pulses occur from the clock 39 without an intervening pulse from the drop detector 19, it is apparent that a drop failed to fall through the drip chamber in response to opening of the valve. Contrariwise, successive pulses received from the drop detector 19 without an intervening pulse from the clock 39, indicate that multiple drops have fallen in response to only a single valve opening. The former condition is defined herein as low rate and the latter as high rate.

In response to the detection of an alarm condition, the alarm detector 46 acts upon the alarm circuitry 49(a) to prevent further energization of the valves 28 and 39, and (b) to produce an alarm indication to inform an attendant that attention is required.

Turning now to the details of the circuitry illustrated in FIG. 5, the variable clock 39 includes a time base oscillator, shown herein as a stable multivibrator 100.

Timing resistors 101 and capacitor 102 establish the frequency of oscillation of the multivibrator, and are adjusted during manufacture to a set frequency, such as 1 Hz. This output frequency, which appears at terminal 103, is coupled to a signal input terminal 104 of a phase locked loop 105. As is well known, phase locked loops are circuits of the type including a phase comparator and a voltage controlled oscillator, being adapted to compare two input signals and produce an output signal having a frequency dependent upon the relationship between the input signals. In the present instance, the time base signal on terminal 104 is compared to a second signal on terminal 106, the output signal on terminal 107 having a frequency dependent upon the relationship between the terminal 104 and 106 signals. It is seen that the signal on terminal 106 is provided by a divide by n counter 108 comprised of least significant digit counter chip 109 and most significant digit counter chip 110.

In accordance with one feature of the invention, the modulus of the counter 108 is made selectable by user accessible digital thumbwheel switches so that an attendant may precisely select a desired number of drops per minute to be administered to a patient. To that end, a pair of thumbwheel switches 111, 112 are provided, such thumbwheel switches having, for example, a BCD output. Accordingly, if the attendant desires, for example, 37 drops per minute, switch 112, the most significant digit, will be set at 3 and switch 111 at 7. It is seen that the binary outputs of the switches 111, 112 are coupled to the associated data inputs of counters 109, 110. The parallel enter terminals 114, 115 of the counters are coupled to the "zero" output 116 of the least significant digit counter 109. Further, the "zero" output 117 of counter 110 is coupled to the carry forward input 118 of counter 109. Finally, the Q4 output of counter 109 is coupled to the clock input of counter 108 so that clocking counter 109 through its complete cycle causes the subsequent clocking of counter 110. The clock input 120 of least significant digit counter 109 is driven by the VCO output 107 of the phase locked loop.

In operation, the thumbwheel switches 111, 112 set a modulus for the divide by N counter 108, the number on the thumbwheel switches being parallel loaded into the counter each time the counter cycles through its preselected number. Thus, for example, if the number 37 is set on the thumbwheel switches after 30 clock pulses applied to terminal 120 the output 117 of counter 110 would change states; after an additional 7 pulses the output 116 of counter 109 would then change state providing a signal to input terminal 106 of the phase locked loop and parallel loading the preset number into the counter for start of another cycle. The phase locked loop 105 attempts to bring the signals on terminals 104 and 106 into synchronism by varying the output frequency on terminal 107 which, it is seen, is fed back to terminal 106 via the divide by N counter. Because the frequency of the signal on terminal 104 is fixed, such as at 1 Hz, the phase locked loop produces a frequency at output terminal 107 which is equal to the base frequency on terminal 104 times the number set on the switches 111, 112. In short, the output of counter 108 taken at teminal 116 must match the 1 Hz signal on terminal 104. Thus, if the thumbwheels are set at the number 62, the output frequency of the phase locked loop at terminal 107 must be 62 Hz in order to provide a 1 Hz signal at terminal 116, coupled to terminal 106 of the phase locked loop for comparison with the 1 Hz base signal. Using two thumbwheel switches and a 1 Hz base frequency, the output of the phase locked loop is variable over the range of 1 to 99 Hz. This output signal is coupled to input terminal 123 of a time base generator 124, such time base generator serving to divide the signal by 60, thereby to produce an output signal at terminal 125 variable in dependence on the setting of the thumbwheel switches in the range between 1 and 99 cycles per minute. The signal at terminal 125 may be considered the base operating frequency of the control circuit, being settable via the digital switches 111, 112 to a frequency equal to the desired drop rate.

As described above, and in practicing the invention, the base operating frequency taken at terminal 125 of the frequency base generator 124 is digitally selectable, such signal being used to control the valve 15 so as to afford an attendant the ability to precisely select a desired drop rate. To that end, the base operating frequency signal on terminal 125 of the time base generator 124 is coupled through a differentiating circuit comprised of NAND gate 127, inverter 128 and timing components 129. Such circuitry serves to produce a narrow negative pulse at the output of NAND gate 127 in response to each positive transition of the base frequency signal at terminal 125.

For energizing the valve magnets 28, 29 in response to such pulse, the output of NAND gate 127 is inverted in inverter 130 and coupled to the set input 131 of flip-flop 132 within the latching circuit 40. Accordingly, the flip-flop 132 is set at the leading edge of each of the clock pulses produced at terminal 125 of the time base generator. The Q output 133 of the flip-flop is coupled to one input of NAND gate 135 and, in conjunction with a high signal on the other input of NAND gate 135 satisfies such gate driving the output thereof low. The low output from NAND gate 135 is coupled to the input of NAND gate 137, causing the output thereof to go high. The high output of NAND gate 137, in turn, provides base current to transistor 139 in the switching circuit 41. As a result, the transistor switch is turned on at the lead edge of each of the base operating frequency pulses and is latched on by the control circuit, in normal operation being reset by the detection of a drop falling through the drip chamber.

The details of the drop detector 19 and pulse shaper 28 will be described below. Suffice it to say for the moment, that the detection of a drop falling through the drip chamber serves to produce a brief positive pulse at the output of amplifier 140. It is seen that the output of amplifier 140 is coupled to input 171 of time base generator 124. The time base generator is a commercially available circuit identified as Motorola Part No. MC14566, and contains, in addition to the divide by 60 counter described above, an independent monostable multivibrator. Input 171 is the trigger input of such monostable, and causes the output terminal 172 to produce a brief positive pulse slightly delayed from the leading edge of each trigger signal. In effect, the monostable portion of time base generator 124 serves as an additional pulse shaper for the drop pulse produced by the drop detector.

For closing the electromagnetically operated valve in response to the detection of a drop, the shaped drop pulse at terminal 172 is coupled to the reset input 174 of the latching flip-flop 132. As a result thereof, the Q output is driven low, causing the output of NAND gate 135 to be driven high, thereby satisfying NAND gate 137, driving the output thereof low, and removing the forward bias from transistor 139, turning off the transistor switch and deenergizing the electromagnets 28, 29.

In summary, during normal operation, the clock circuitry functions to produce at terminal 125 of the time base generator a digital signal having a frequency equal to the desired drop rate. The transistor switch 41 is latched on by the base operating frequency signal, such as at the lead edge thereof, and remains on until a drop is sensed by the drop detector 19. The sensing of a drop produces a pulse which serves to reset the latching circuitry and deenergize the transistor switch 41. The transistor switch 41 is thereby prepared for reenergization in response to the leading edge of the next clock pulse.

For indicating normal operation to an attendant or the like, a drop indicator 44 is provided, responsive to pulses produced by the drop detector for flashing an LED mounted on the system control panel. To that end, a drop pulse extender 42 including a conventional monostable multivibrator 180 and its associated timing components 181 has a trigger input 182 coupled to the output of amplifier 140. The output of the monostable, taken at terminal 183 drives the base-emitter circuit of transistor 184, thereby to illuminate LED 185. The timing components 181 are adjusted so that the drive signal to the transistor 184 is present for a sufficient period to illuminate indicator 185 making it visible to an observer.

To provide an overriding safety feature, the circuitry is adapted to establish a maximum period during which the electromagnetic valve may be energized, and to deenergize the valve at the termination of such period. To that end, a retriggerable multivibrator 190 having associated timing components 191 is provided, triggered from the base operating frequency timing pulse produced at the output of NAND gate 127, and having a period set to the desired maximum open time, such as two seconds. It is seen that each magnet energizing pulse produced at the output of NAND gate 127 serves to retrigger the multivibrator 190, restarting the timing period thereof. The output 193 of the multivibrator is coupled to the input of NAND gate 135, the second input being coupled to the Q output of flip-flop 132 as described above. As a result, so long as the multivibrator 190 remains in its triggered state, setting of the flip-flop 132 will serve to satisfy NAND gate 135 and energize the valve as described above. However, should the valve stay continuously energized for a period exceeding the pre-established period of multivibrator 190, the output 193 thereof will switch low, driving the output of NAND gate 135 high and deenergizing the valve.

To detect abnormal conditions and to inhibit further energization of the valve in response thereto, alarm detector 46 and alarm 49 monitor the signals from the clock and from the drop detector to assure that such signals alternate. Before describing the alarm detector 46 in detail, the alarm 49, itself, and its function in inhibiting energization of the valve will be described. Suffice it to say for the moment, that the detection of an alarm condition causes the alarm 46 to produce a positive signal at output 200 thereof. This positive signal is coupled to the clock input 201 of flip-flop 202 in the alarm circuitry. Because the D input 203 of such flip-flop is coupled to the positive supply of voltage, the clock pulse will drive the Q output 204 high and the $\bar{Q}$ output 205 low. It is seen that the Q output is coupled to the reset input 207 of the time base generator 124, and serves to hold the divide by 60 counter in reset, thereby preventing further magnet energizing clock pulses from being generated at the terminal 125. As a result, no further clock pulses will pass the time base generator 124, precluding the changing of state of the flip-flop 132 as well as the retriggering of the two second limit circuit 190. If the alarm condition were caused by a high rate condition, the sensing of the first drop would have reset flip-flop 132, as described above, deenergizing the valve at that time; the alarm then locks the timing generator, preventing reenergization of the valve. If the alarm condition were caused by a low rate condition, the flip-flop 132 would have been left in its set condition; in that case, the valve will remain open until the period of timer 190 expires, at which point that timer will deenergize the valve. As noted above, the circuitry, in the alarm condition, will be prevented from retriggering the timer 190, thus assuring that the control circuit is latched in the alarm condition.

Having thus produced a mode of operation wherein the flip-flop which controls the latch (flip-flop 132) is left in one or the other of its stable states in an alarm condition in dependence upon the type of condition which caused the alarm, such flip-flop is used for a second purpose in driving the alarm circuitry. To that end, NOR gates 210, 211 are provided, with one of the inputs of NOR gate 210 being coupled to the Q output of flip-flop 132, and one of the inputs of NOR gate 211 being coupled to the $\bar{Q}$ output thereof. One of the inputs of each of the NOR gates 210, 211 is coupled to the $\bar{Q}$ output of alarm flip-flop 202. In the normal condition, the $\bar{Q}$ output of flip-flop 202 will be high, keeping the outputs of both NOR gates 210 and 211 low, keeping the alarm circuitry inactive. However, when flip-flop 202 is clocked into the alarm condition, the $\bar{Q}$ output is driven low with the result that one of gates 210 or 211 will drive its output high. Which of the gates 210 or 211 responds is determined by the condition in which flip-flop 132 is left. If flip-flop 132 last "saw" a set pulse (derived, it is recalled, from the valve opening clock) the Q output will be high and the $\bar{Q}$ low. As a result, NOR gate 210 will maintain its output in a low condition but NOR gate 211 will switch its output high, turning on transistor 212 and illuminating indicator 213. Recalling that two successive clock pulses without an intervening drop pulse indicate a low rate condition, it will be appreciated that indicator 213 is the low rate indicator. In the event flip-flop 132 last saw a reset pulse (derived, it is recalled, from the drop detector), NOR gate 210 will drive its output high, causing transistor 214 to conduct and illuminating high rate indicator 215. A NAND gate 216 has inputs coupled to the collectors of transistors 212 and 214, and an output driving transistor 217, having audible alarm 218 in its load circuit. As a result, if either the low rate or the high rate alarm 213 or 215 is energized, the NAND gate 216 will respond by also energizing the audible alarm 218. The NOR gates 210, 211 each have a third input coupled to the output 103 of the 1 Hz oscillator. In the alarm mode, therefore, the alarm indicator and the audible alarm will cycle on and off at a 1 Hz rate.

In accordance with one feature of the invention, means are provided for digitally counting errors (i.e. missed drops or excess drops) and causing the control system to enter the alarm mode only after a predetermined number of errors are detected. It should be noted that the term error as used herein indicates a single missed drop or a single excess drop.

In accomplishing the foregoing, the alarm detector 46 includes an error counter in the form of binary counter 220 having three of its binary outputs 221 coupled to a multiplexer 222, the multiplexer providing the aforementioned alarm detector output 200. The counter 221 has a clock input driven by NAND gate 224. The inputs of NAND gate 224 are normally maintained in the high condition, keeping the output thereof low. However, in response to a valve opening clock pulse produced at terminal 125 of the time base generator 124, the output of NAND gate 127 will be temporarily driven low, causing the output of NAND gate 224 to be temporarily driven high and clocking the counter 220. Similarly, drop pulses are coupled through the circuitry including inverter 226 and NAND gate 227 for temporarily driving the associated input of NAND gate 224 low thereby to clock the counter 220. Finally, it is seen that the reset input of counter 220 is driven by a NAND gate 229 having a first input coupled to the $\overline{Q}$ output of the alarm flip-flop 202 and therefore normally maintained high, and a second input driven by a timing circuit responsive to the cyclic closing of the valve including NAND gate 230, inverter 231 and timing components 232. It is seen that these latter components are driven from the $\overline{Q}$ output of latching flip-flop 132 and are connected so as to produce a brief positive pulse each time the flip-flop 132 is returned to its reset condition. Accordingly, during normal operation, each time the flip-flop 132 is reset (responsive to the detection of a drop) a brief pulse is produced at the output of NAND gate 230 which acts through NAND gate 229 to reset the counter 220. Accordingly, during normal operation, the counter 220 will count both clock pulses and drop pulses, but will be cyclically reset upon sensing of each drop so that the count within the counter will never exceed a known value during normal operation.

The alarm circuitry including error counting functions substantially as follows. Assuming the counter 220 begins in its reset or zero condition, production of a valve opening pulse at terminal 125 of the time base generator 124, in addition to opening the valve as described above, acts upon NAND gate 224 to couple a clock pulse to the counter 220, bringing the count within the counter to one. A drop forms and falls, and is detected by the drop detector 19 which acts through the pulse shaper 38 to produce a brief positive pulse at the output of amplifier 140. This positive pulse accomplishes two functions. Initially, it acts through NAND gate 227 and 224 to clock the counter 220, thereby leaving a count of two within such counter. Secondly, the pulse triggers the astable section of time base generator 124 producing a brief positive pulse of short duration delayed slightly from the triggering pulse but occurring within the period of the longer triggering pulse. As a result, the output of NAND gate 227 will be driven low upon detection of a drop, will return high at the start of the pulse produced by the multivibrator at terminal 172 thereof, will be driven low again at the termination of such pulse, and will return high at the termination of the drop pulse produced at the output of amplifier 140. These pulses act upon the counter as follows. Recalling that the count of one is stored in the counter 220 in response to the valve opening pulse produced at terminal 125, the detection of a drop, producing the first negative transition at the output of NAND gate 227 will act through NAND gate 224 to clock the counter 220 to the count of two. Following this, the brief positive pulse will be produced at terminal 172 of the multivibrator. This pulse will serve to reset the flip-flop 132 which will act through the timing circuit including inverter 231 and NAND gate 230 to reset the counter 220 and hold such counter in reset during the time the second negative pulse is produced at the output of NAND gate 227. Accordingly, the second pulse, during normal operation, will not be counted and the counter 220 will cycle as follows: 0, 1, 2, 0, 1, 2, etc.

In the low rate or no drop condition, the circuitry will be incapable of producing a reset pulse for counter 220, and accordingly the counter will continue to count valve opening pulses produced at terminal 125. Because each of these pulses without an intervening drop pulse is considered an error, the counter 220 will therefore be adapted to count errors. In this mode, the first valve opening pulse will bring the counter to a count of one, the first error to a count of two, the second error to a count of three, and so on. The multiplexer 222 is coupled to the 3, 4 and 5 outputs of the counter and selectively couples these counter outputs to the multiplexer output 200 for causing the circuitry to enter the alarm mode. In accordance with one feature of the invention, which of the outputs actuates the alarm mode is made dependent upon the setting of a digital switches 111, 112. It is seen that the selector inputs 240, 241 and 242 of the multiplexer 222 are coupled to the most significant digit switch 112 for selecting which of the multiplexer inputs are coupled to the output 200 thereof. The 1, 2, 4 and 8 outputs of the switch 112 are coupled through decoding circuitry including NOR gate 244 and inverter 245 to the A, B and C inputs of the multiplexer 222 so that for all settings of the digital switches 111, 112 between 1 and 9, the 3 output of the counter 220 will be coupled to the multiplexer output 200, for all settings between 10 and 19, the 4 output will be selected and for all settings above 20, the 5 output will be selected. Accordingly, for low drip rates, selected between 1 and 9 drops per minute, one error will serve to cause the control circuit to enter the alarm mode, since the first clock pulse will set the counter 220 at 1, the second clock pulse absent an intervening drop pulse will set the counter at 2, and either a following drop pulse or a succeeding clock pulse absent any intervening drop pulse will drive the counter to 3, thus putting the circuit in the alarm mode. Similarly, at settings between 10 and 19 drops per minute, two successive errors will be required to cause the circuitry to enter the alarm mode. For all settings between 20 and 99 drops per minute, three successive errors are required to cause the circuitry to enter the alarm mode. As a result, the circuit is very sensitive at low drop rates and increases the deadband for higher drop rates so that sufficient protection is afforded at lower drop rates while sensitivity it decreased at higher drop rates where additional errors might be tolerated. The mode of operation thus achieved is very desirable because drops occasionally fail to fall because of temporary conditions, such as an increase in back pressure which might be caused when the patient changes his position. Such occurrences are of little practical consequence, especially at high drop rates. Accordingly the control system ignores these inconsequential errors, avoiding premature alarm conditions, while still providing the necessary sensitivity at low drop rates.

The circuitry acts in a fashion similar to that described above to count high drop rate errors. Recalling that the first valve opening pulse will cycle the counter 220 to the count of 1, the detection of a first drop will serve to clock the counter 220 to the count of 2 and then to reset the counter to a count of zero. If another drop is detected before the occurrence of a valve opening pulse at terminal 125, the counter 220 will be clocked to the count of 1 by the first brief pulse at the output of NAND gate 227 and then to the count of 2 by the second brief pulse at the output thereof. Accordingly, the counter 220, just as in the case of low drop rates is cycled to the count of 2 at the detection of the first error. If a further drop is then sensed before the occurrence of a valve opening clock pulse, the counter 220 will be clocked further to the count 3, then 4, causing the system to enter the alarm mode if set in the relatively low drop rate, such as below 20 drops per minute. If still another drop is detected before the occurrence of a valve opening pulse, the counter 220 will be clocked still further to the count of 5, causing the system to enter the alarm mode even if the attendant has selected a high drop rate.

As an alternative to the permanent magnet flushing means described above, the circuit illustrated in FIG. 5 provides means for electronically flushing the system, shown herein as flush pushbutton 250 and its associated circuitry. It is seen that an inverter 251 has its input coupled through a resistor 252 to ground and through normally open flush switch 250 to a positive supply of voltage. As a result, the output of inverter 251 is normally maintained at a high level, allowing NAND gate 137 to respond to the low level from NAND gate 135 to energize the electromagnets and open the valve under the supervision of the latching circuit. When it is desired to manually flush this system the flush switch 250 is closed, driving the output of inverter 251 low which, in turn, drives the output of NAND gate 137 high, causing transistor 139 to conduct, energizing the electromagnets 28, 29 and opening the valve. The valve will remain open as long as the flush switch 250 remains closed.

In addition to opening the valve, the high level conducted through the switch 250 is coupled to the reset input of alarm flip-flop 202 to override any clock pulses resulting from error detection and to prevent the system from entering the alarm mode. Thus, control of the circuit is completely under the switch 250, and the alarm functions, both display and inhibiting, are disabled. Further, a capacitor 254, paralleling the flush switch 250 drives the alarm flip-flop 202 to its reset condition when the circuit is first switched on.

It should also be noted that the power supply for the circuit illustrated in FIG. 5 is preferably of the a.c.-d.c. variety. For example, a typical nickel cadmium rechargeable circuit, including a nickel cadmium battery coupled across a bridge rectifier in the secondary of a power supply transformer circuit, acts as a filter during a.c. operation and comprises a source of power when the a.c. supply is removed. As a result, the electronic IV control may operate in stationary installations in the patient's room when powered from the 110 a.c. outlet, and, by virtue of the d.c. power supply, when the a.c. power is not available, as for example when the patient is being transported or when the a.c. power is lost for some reason.

Turning now to the circuitry of the drop detector illustrated at the left hand portion of FIG. 5, there is provided a light emitter and light sensor responsive thereto, shown herein as light emitting diodes 141 and phototransistor 142. As noted above, these elements are arranged in the drop detector housing 19 in opposed relationship and in optical communication so that the light beam produced by the emitter 141 is received by the detector 142 in such a way that any drop falling through the drip chamber will interrupt at least a portion of the light beam and thereby be sensed by the detector.

Ignoring for the moment the circuitry controlling the bias on the light emitter 141, and assuming merely that the emitter is functioning to produce a beam of light, the emitted light received by the sensor 142 will cause the sensor to conduct in accordance with the light intensity. It is seen that the sensor 142 is coupled in the negative feedback path of an operational amplifier 144. In normal operation, with no drops falling, the output of amplifier 144 will be held at a steady intermediate level. However, when a drop is sensed, the impedance of the sensor 142 increases, thereby decreasing the amount of negative feedback around the amplifier 144 and causing the output thereof to swing positively. This positive pulse is coupled to the pulse shaper 38, and specifically to the inverting input of an amplifier 145 therein. The amplifier 145 and the associated amplifier 140 are arranged so that the positive pulse coupled to the inverting input of amplifier 145 generates a brief positive pulse at the output of amplifier 140. When the positive pulse coupled to the inverting input of amplifier 145 exceeds the level on the non-inverting input, the amplifier 145 will drive its output sharply toward ground. This signal is differentiated by capacitor 146 coupled between amplifier 145 and the inverting input of amplifier 140. As a result, the amplifier 140 will drive its output sharply positive. Positive feedback through resistor 147 and diode 148 provides a sharp pulse at the output of amplifier 140. After capacitor 146 charges to a sufficient level, the output of amplifier 140 will switch back toward ground, the positive feedback through resistor 147 enhancing the sharpness of the switching. Accordingly, a brief sharply defined positive pulse is produced at the output of the pulse shaper for each drop sensed in the drip chamber.

In accordance with one feature of this aspect of the invention, the light emitter is provided with means for adjusting the intensity thereof, such intensity being adjusted in dependence upon the average amount of light incident upon the sensor 142. To that end, the power supply for the light emitter 141 includes a transistor 150 having an emitter resistor 151. The output of the sensing amplifier 144 is coupled to the non-inverting input of a sensititivity adjusting amplifier 152. A resistor interposed between the output of amplifier 144 and the input of amplifier 152, and a capacitor coupled from said input to ground serves to make the amplifier responsive to the quiescent radiation incident on the sensor but insensitive to momentary changes, such as those caused by the sensing of a drop. Accordingly, the voltage at the non-inverting input of amplifier 152 is an indication of the average light incident upon the sensor 142 and drives the transistor 150, having its emitter coupled to the inverting input of amplifier 152, to maintain a desired level of illumination by the light emitters 141. If the average light incident upon the sensor decreases, such as might be caused by fogging of the drip chamber, the voltage at the inverting input of amplifier 152 rises, causing the amplifier 152 to drive the transistor 150 harder and increasing the current flow through the light emitters 141. This serves to increase the light level which, in turn, reduces the voltage at the inverting input of amplifier 152 until a quiescent condition results.

Thus, the sensor 142 not only serves to detect each drop as it falls through the drip chamber, but additionally adjusts the associated light source so that sufficient sensitivity is maintained over all operating conditions, including those wherein the drip chamber is fogged. It is of further note that the emitter of transistor 150 is connected to the non-inverting input of amplifier 145 and thus provides an accurate measure of average incident light as a reference against which drops are detected.

Turning finally to FIGS. 6-10, there is shown the structure of the drop detector, the circuitry of which is illustrated in FIG. 5. As with the detector described in connection with FIG. 2, the illustrated drop detector 19a is preferably formed of molded plastic and comprises a generally U-shaped housing 21a having an elongated slot 22a in one side thereof, with a generally U-shaped channel or groove 23a in the body extending around the slot 22a adjacent the upper portion thereof. In the present embodiment the light source comprises a plurality of light emitters 141, shown here as four in number, arranged in line along the slot 22a and aimed toward the light detector 142, so as to completely illuminate the associated portion of the drip chamber when the drip chamber is positioned in the housing. The light detector 142 is located at the rear end of a horizontal channel 160 so as to restrict the field of view of the sensor 142 to the general elevation occupied by the light emitters 141. Accordingly, the sensor 142 has a relatively narrow vertical field of view but a horizontal field of view encompassing the entire diameter of the drip chamber. This limited vertical field of view in connection with the extended horizontal field of view and the extended horizontal field of illumination provided by the array of emitters 141 yields an arrangement wherein drops are detected irrespective of where in the drip chamber they ultimately fall.

To further increase the effectiveness of the illustrated drop detector, means are provided to make the detector insensitive to ambient light and especially sensitive to light emitted by the photo-diodes 141. To that end, the light emitter is comprised of photo-diodes of the infrared emitting type, the light sensor is of the type responsive to infrared radiation, and an infrared filter 161, designed to filter all but infrared illumination is disposed across the face of the sensor 142. In this way, the drop detector operates and responds only to illumination or radiation emitted internally, and is insensitive, both in its detecting and self-adjusting features, to ambient illumination external of the housing 21a. When infrared or other non-visible illumination and sensing are employed, it is preferred to include a further light emitting diode 162 in the housing 21a, such diode emitting light in the visible spectrum to provide an indication to an attendant that the drop detector is operational. The light emitting diode 162 is also illustrated in FIG. 5; such diode receiving a fixed bias because the level of illumination produced thereby is not critical.

As seen more particularly in FIGS. 9 and 10, the light emitters 141 are supported in a two-part chassis 253 comprising an upper chassis part 254 having a plurality of semicylindrical emitter receiving grooves 255 and a channel defining slot 256 in one surface thereof. A lower chassis part 257 has a plurality of like semicylindrical emitter receiving grooves 258 therein and a channel defining slot 259. The photosensitive means 142 is confined in a socket defined by a pair of identical semicylindrical recesses 260 and 261 in opposed confronting surfaces of upper and lower photosensor housing parts 262 and 263, respectively, which are suitably secured to the end surfaces of upper and lower chassis parts 254 and 257.

Moreover, in some instances a drop rate of about 40 drops per minute and greater may be required. With such a high drop rate, there is a very short amount of time between clock pulses and the error counter may not accumulate enough error counts to go into alarm, and accordingly, an error accumulator is provided in the circuit to accumulate the error signals, so that when a predetermined number of error counts, as, for example, 8, have been accumulated, the circuit goes into its alarm mode.

It will now be apparent that what has been provided is a novel IV set wherein means are provided for allowing an attendant to digitally select a desired drop rate, and providng digital circuitry for operating the IV valve at the selected drop rate. In the illustrated embodiment, the drop rate may be changed in one drop increments from 1 through 99 drops per minute. Additionally, the system is provided with an alarm indicator and uses the state of the magnet driving flip-flop to differentiate between high and low rate alarms. The characteristics of the alarm system are further enhanced by providing digital error counting, thereby making the alarm system very sensitive at low selected drip rates, but providing an increased deadband at higher drip rates. Finally, an improved drop detector is provided wherein the sensor not only detects drops falling through the drip chamber, but automatically adjusts the associated light emitter to maintain a desired level of illumination incident upon the sensor.

We claim:

1. An intervenous infusion set for use with a supply of intravenous fluid, said set comprising in combination, a drip chamber adapted to be connected to said supply, a length of IV tubing connected to said drip chamber and forming with said drip chamber a fluid flow passage, valve means within said passage, electromagnetic valve operating means associated with said valve means, drop detector means associated with said drip chamber for sensing drops falling therethrough, a variable frequency clock, digital switch means coupled to said clock for digitally selecting the output frequency of said clock, said variable frequency clock including a time base generator having a preset frequency, a variable modulus counter, said digital switch means being coupled to said counter for allowing an attendant to select the modulus thereof, and means for multiplying said preset frequency by the selected modulus of said counter for digitally selecting the output frequency of said clock, whereby a desired drop rate may be selected by manipulation of the digital switch means, switch means coupled to said valve operating means for controlling energization of said valve operating means, circuit means coupling said clock to said switch means for actuating said switch means to energize the valve operating means to open the valve at the rate selected by said digital switch means, said circuit means including means responsive to said drop detector means for deactuating said switch means to deenergize the valve operating means and thus enable said valve to close upon sensing of a drop by said drop detector means, and alarm means for detecting errors in the drop rate from that set on said digital switch means and entering an alarm mode in response thereto, said alarm means including means for preventing energization of said switch means whenever said alarm means is in said alarm mode.

2. An intervenous infusion set for use with a supply of intravenous fluid, said set comprising in combination, a drip chamber adapted to be connected to said supply, a length of IV tubing connected to said drip chamber and forming with said drip chamber a fluid flow passage, valve means within said passage, electromagnetic valve operating means associated with said valve means, drop detector means associated with said drip chamber for sensing drops falling therethrough, a variable frequency clock, digital switch means coupled to said clock for digitally selecting the output frequency of said clock, said variable frequency clock including a phase locked loop, a time base generator for supplying a preset frequency to said phase locked loop, a variable modulus counter in a feedback path between an output and a second input of said phase locked loop, said digital switch means being coupled to said variable modulus counter for selecting the modulus thereof, whereby the output frequency of said phase locked loop is equal to the base frequency at said first input multiplied by the selected modulus of said counter, switch means coupled to said valve operating means for controlling energization of said valve operating means, circuit means coupling said clock to said switch means for actuating said switch means to energize the valve operating means to open the valve at the rate selected by said digital switch means, said circuit means including means responsive to said drop detector means for deactuating said switch means to deenergize the valve operating means and thus enable said valve to close upon sensing of a drop by said drop detector means, and alarm means for detecting errors in the drop rate from that set on said digital switch means and entering an alarm mode in response thereto, said alarm means including means for preventing energization of said switch means whenever said alarm means is in said alarm mode.

3. An intravenous infusion set for use with a supply of intravenous fluid, said set comprising in combination, a drip chamber adapted to be connected to said supply, a length of IV tubing connected to said drip chamber and forming with said drip chamber a fluid flow passage, valve means within said passage, electromagnetic valve operating means associated with said valve means, drop detector means associated with said drip chamber for sensing drops falling therethrough, a variable frequency clock, digital switch means coupled to said clock for digitally selecting the output frequency of said clock, switch means coupled to said valve operating means for controlling energization of said valve operating means, circuit means coupling said clock to said switch means for actuating said switch means to energize the valve operating means to open the valve at the rate selected by said digital switch means, said circuit means including means responsive to said drop detector means for deactuating said switch means to deenergize the valve operating means and thus enable said valve to close upon sensing of a drop by said drop detector means, and alarm means for detecting errors in the drop rate from that set on said digital switch means and entering an alarm mode in response thereto, said alarm means including means for preventing energization of said switch means whenever said alarm means is in said alarm mode, said circuit means including bistable means having a first and second stable state, means responsive to the variable frequency clock for switching said bistable means to its first stable state, means responsive to the drop detector means for returning said bistable means to its second stable state, coupling means interposed between the bistable means and the switch means for energizing said switch means to open said valve when said bistable means is in its first stable state, said alarm means including means for disabling said coupling means and preventing further switching of said bistable means in said alarm mode, and alarm indicator means responsive to the state of said bistable means and said alarm means for indicating high rate and low rate errors in said alarm mode in dependence upon the last state of said bistable means.

4. An intravenous infusion set for use with a supply of intravenous fluid, said set comprising in combination, a drip chamber adapted to be connected to said supply, a length of IV tubing connected to said drip chamber and forming with said drip chamber a fluid flow passage, valve means within said passage, electromagnetic valve operating means associated with said valve means, drop detector means associated with said drip chamber for sensing drops falling therethrough, said drop detector means including light emitting means for illuminating at least a portion of said drip chamber, photosensor means opposed to said light emitting means for sensing the light from said light emitting means passing through said drop chamber, first circuit means driven by said photosensor means and responsive to the average light sensed by said photosensor means for regulating the intensity of said light emitting means, and second circuit means driven by said photosensor means and responsive to sudden transitions in light sensed by said photosensor means for producing a drop signal in response to the detection of a drop, whereby said photosensor serves the dual function of detecting drops and compensating for varying levels of illumination received thereby, a variable frequency clock, digital switch means coupled to said clock for digitally selecting the output frequency of said clock, switch means coupled to said valve operating means for controlling energization of said valve operating means, circuit means coupling said clock to said switch means for actuating said switch means to energize the valve operating means to open the valve at the rate selected by said digital switch means, said circuit means including means responsive to said drop detector means for deactuating said switch means to deenergize the valve operating means and thus enable said valve to close upon sensing of a drop by said drop detector means, and alarm means for detecting errors in the drop rate from that set on said digital switch means and entering an alarm mode in response thereto, said alarm means including means for preventing energization of said switch means whenever said alarm means is in said alarm mode.

5. The intravenous infusion set as set forth in claim 4, wherein the light emitting means is of the type emitting light in the non-visible spectrum, said photosensor means including means for preventing said photosensor means from responding to light in the visible spectrum, whereby said photosensor means is insensitive to ambient illumination.

6. An intravenous infusion set for use with a supply of intravenous fluid, said set comprising in combination, a drip chamber adapted to be connected to said supply, a length of IV tubing connected to said drip chamber and forming with said drip chamber a fluid flow passage, valve means within said passage, electromagnetic valve operating means associated with said valve means, drop detector means associated with said drip chamber for sensing drops falling therethrough, a variable frequency clock, digital switch means coupled to said clock for digitally selecting the output frequency of said clock, switch means coupled to said valve operating means for controlling energization of said valve operating means, circuit means coupling said clock to said switch means for actuating said switch means to energize the valve operating means to open the valve at the rate selected by said digital switch means, said circuit means including means responsive to said drop detector means for deactuating said switch means to deenergize the valve operating means and thus enable said valve to clsoe upon sensing of a drop by said drop detector means, and alarm means for detecting errors in the drop rate from that set on said digital switch means and entering an alarm mode in response thereto, said alarm means including means for preventing energization of said switch means whenever said alarm means is in said alarm mode, said alarm means including counter means for counting said errors, selector means responsive to the setting on said digital switch means for determining the number of errors required to enter said alarm mode, said selector means being so arranged and constructed to increase the number of errors required to enter the alarm mode with increasing drop rates set on said digital switch means.

7. An intravenous infusion set for use with a supply of intravenous fluid, said set comprising in combination, a drip chamber adapted to be connected to said supply, a length of IV tubing connected to said drip chamber and forming with said drip chamber a fluid flow passage, valve means in the passage for controlling flow of fluid in said passage, circuit means including a timer for opening the valve means at a preselected rate to cause the falling of drops at said rate, and drop detector means associated with said drip chamber and operative upon said circuit means for closing the valve in response to sensing of a drop falling through said drip chamber, said drop detector means including light emitting means at one side of the drip chamber for illuminating at least a portion of said drip chamber, photosensor means at the other side of the drip chamber in opposed relation to said light emitting means for sensing the light from said light emitting means passing through said drip chamber, first circuit means driven by said photosensor means and responsive to the average light sensed by said photosensor means for regulating the intensity of said light emitting means, and second circuit means driven by said photosensor means and responsive to sudden transitions in light as produced by a falling drop and sensed by said photosensor means for producing a drop signal in response to the detection of a drop, whereby said photosensor means serves the dual function of detecting drops and compensating for varying levels of illumination received thereby.

8. The intravenous infusion set as set forth in claim 7, wherein the light emitting means is of the type emitting light in the non-visible spectrum, said photosensor means including means for preventing said photosensor from responding to light in the visible spectrum, whereby said drop sensor is insensitive to ambient illumination.

9. The intravenous infusion set as set forth in claim 7, wherein said first circuit means further includes means for preventing said first circuit means from responding to sudden transitions in said light sensed by the photosensor means, whereby the intensity of said light emitting means is unaffected by detection of drops falling through said drip chamber.

10. The intravenous infusion set as set forth in claim 7, wherein said drop detector means includes a housing, said light emitting means including an array of individual light emitters mounted in said housing in a generally horizontal orientation to illuminate the width of said drip chamber, said photosensor means being mounted in said housing and set back from said drip chamber by a channel restricting the vertical field of view of said photosensor but providing a horizontal field of view encompassing the width of said drip chamber.

11. The intravenous infusion set as in claim 10, wherein an emitter supporting chassis is supported in said housing, said chassis including a plurality of sockets receiving respective light emitters and an opposed socket receiving a single photosensor, said array of light emitters focused on the photosensor across the drip chamber and through the channel.

12. The intravenous infusion set as in claim 11, wherein a further light emitter of the type emitting light in the visible spectrum is in said housing adjacent the array of light emitters for giving a visual indication of the operability of said drop detector means.

13. The intravenous infusion set as in claim 12, wherein said chassis comprises a plurality of secured together parts, including a top half and a bottom half, said halves having mating confronting recesses therein defining said sockets and channel.

14. An intravenous infusion set for use with a supply of intravenous fluid, said set comprising in combination, a drip chamber adapted to be connected to said supply, a length of IV tubing connected to said drip chamber and forming with said drip chamber a fluid flow passage, valve means in said passage for controlling flow of fluid therethrough, electromagnetic valve operating means associated with said valve, drop detector means associated with said drip chamber for sensing drops falling therethrough and producing drop pulses in response thereto, a variable frequency clock, drop rate selector means coupled to said clock for selecting the output frequency of said clock to produce clock pulses having a frequency equal to the desired drop rate, switch means coupled to said valve operating means for controlling said valve means, circuit means responsive to said clock pulses for energizing said switch means to open the valve means at the rate selected by said drop rate selector means, said circuit means including means responsive to said drop pulses for deenergizing said switch means to close said valve means upon sensing of a drop by said drop detector, whereby in normal operation clock pulses and drop pulses alternate, and alarm means responsive to said clock pulses and drop pulses for detecting errors in the form of non-alternation between said pulses, said alarm means including counter means for counting said errors, means associated with said counter means for selectively establishing a maximum number of allowable errors dependent upon the selected drop rate and entering an alarm mode in response to said counter means counting a number of errors exceeding said maximum number, and means for preventing energization of said switch means in said alarm mode.

15. The intravenous infusion as set forth in claim 14, wherein said counter means includes a binary counter for counting said drop pulses and said clock pulses, and circuit means operative upon said binary counter for resetting same in response to the alternate occurrence of clock pulses and drop pulses.

16. The intravenous infusion set as set forth in claim 14, wherein said counter associated means is a multiplexer responsive to the selected drop rate for increasing said maximum number with increasing selected drop rates, thereby to avoid premature entry of said alarm mode.

17. The intravenous infusion set as set forth in claim 16, wherein said drop rate selector includes digital switch means for digitally selecting the output frequency of said clock, said multiplexer having selector inputs coupled to said digital switch means for varying said maximum number in accordance with the drop rate selected by said digital switch means.

18. A drop detector for sensing drops falling through a drip chamber, said drop detector comprising in combination, a housing having means for supporting the drop detector adjacent a drip chamber, light emitting means supported in the housing for illuminating at least a portion of a drip chamber, photosensor means supported in the housing in opposed relation to said light emitting means for sensing the light from said light emitting means passing through a drip chamber, first circuit means connected with the light emitting means and photosensor means to be driven by said photosensor means and responsive to the average light sensed by said photosensor means for regulating the intensity of said light emitting means, and second circuit means connected to be driven by said photosensor means and responsive to sudden transitions in light as caused by a falling drop and sensed by said photosensor means for producing a drop signal in response to the detection of a drop, whereby said photosensor means serves the dual function of detecting drops and also compensating for gradually varying levels of illumination received thereby.

19. The drop detector as set forth in claim 18, wherein the light emitting means is of the type emitting light in the non-visible spectrum, said photosensing means including means for preventing said photosensor means from responding to light in the visible spectrum, whereby said drop sensor is insensitive to ambient illumination.

20. The drop detector as set forth in claim 18, wherein said light emitting means is of the type emitting radiation in the infrared spectrum, filter means carried by the housing in a position to be disposed between a drip chamber and the photosensor means for allowing the passing of infrared radiation to the photosensor means but blocking visible illumination therefrom, whereby said drop sensor is insensitive to ambient illumination.

21. The drop detector as set forth in claim 18, wherein said first circuit means further includes means for preventing said first circuit means from responding to sudden transitions in said light sensed by the photosensor means, whereby the intensity of said light emitting means is unaffected by detection of drops falling through a drip chamber.

22. The drop detector as set forth in claim 18, wherein said light emitting means includes an array of individual light emitters mounted in said housing in a generally horizontal orientation to illuminate the width of a drip chamber, said photosensor means being mounted in said housing in a position to be set back from a drip chamber associated therewith by a channel restricting the vertical field of view of said photosensor means but providing a horizontal field of view encompassing the width of said drip chamber.

23. An intravenous infusion set for use with a supply of intravenous fluid, said set comprising in combination, a drip chamber adapted to be connected to said supply, a length of IV tubing connected to said drip chamber, valve means within said tubing, electromagnetic valve operating means associated with said valve, drop detector means associated with said drop chamber for sensing drops falling therethrough and producing drop pulses in response thereto, a preset time base generator, a variable modulus counter, means coupling said time base generator and variable modulus counter for producing clock pulses at a base operating frequency equal to the preset frequency multiplied by the modulus of said counter, digital switch means connected with said counter for allowing an operator to select the modulus of said counter, bistable means having a first and a second stable state, means coupling said base operating frequency to said bistable means for switching said bistable means to its first stable state, means coupling the drop detector means to said bistable means for returning said bistable means to its second stable state in response to sensing of a drop, switch means coupled to said valve operating means for controlling said valve, coupling means interposed between said bistable means and switch means for energizing said switch means when said bistable means is in its first stable state, alarm means responsive to said base operating frequency pulses and said drop pulses and maintained in a first condition in response to alternation between said pulses, means for detecting errors in the form of non-alternation between said pulses and entering an alarm mode in response thereto, means operative in said alarm mode for deenergizing said coupling means for preventing further energization of said valve switch means, and alarm indicator means responsive to said bistable means and operative in said alarm mode to differentiate between and indicate high rate and low rate alarms.

24. The intravenous infusion set as set forth in claim 23, wherein said alarm means further includes counter means for counting said errors, multiplexing means coupling said counter means to said digital switch means to determine the number of counted errors required to enter said alarm mode, said multiplexing means serving to increase the deadband of errors necessary to enter the alarm mode at drip rates above a preselected minimum.

25. The intravenous infusion set as set forth in claim 24, wherein said counter means includes means for counting said clock pulses and drop pulses, and means for cyclically resetting said counter means in response to the return of said bistable means to said second stable state.

* * * * *